(12) United States Patent
Waechtler et al.

(10) Patent No.: US 10,160,758 B2
(45) Date of Patent: Dec. 25, 2018

(54) METHOD FOR THE PRODUCTION OF PRAZIQUANTEL

(71) Applicant: MERCK PATENT GMBH, Darmstadt (DE)

(72) Inventors: Andreas Waechtler, Darmstadt (DE); Hadia Saleh-Kassim, Forbach (FR); Christian Jasper, Seligenstadt (DE); Joern Kolb, Arheiligen (DE); David Maillard, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

(21) Appl. No.: 15/528,282

(22) PCT Filed: Nov. 17, 2015

(86) PCT No.: PCT/EP2015/002296
§ 371 (c)(1),
(2) Date: May 19, 2017

(87) PCT Pub. No.: WO2016/078758
PCT Pub. Date: May 26, 2016

(65) Prior Publication Data
US 2018/0155339 A1  Jun. 7, 2018

(30) Foreign Application Priority Data
Nov. 21, 2014 (EP) .................... 14003934

(51) Int. Cl.
*C07D 471/04* (2006.01)
*C07C 31/30* (2006.01)
*C07B 55/00* (2006.01)
*C07B 57/00* (2006.01)

(52) U.S. Cl.
CPC ............ *C07D 471/04* (2013.01); *C07B 55/00* (2013.01); *C07B 57/00* (2013.01); *C07C 31/30* (2013.01); *C07B 2200/07* (2013.01)

(58) Field of Classification Search
CPC .................................................... A61K 31/498
See application file for complete search history.

(56) References Cited

PUBLICATIONS

Muneer, et al., Plos One, XP055246218, vol. 4, No. 10, p. e47224 (2012).*
Ebbers, et al., Tetrahedron, vol. 53, No. 28, pp. 9417-9476, XP004105880 (1997).*
International Search Report for PCT/EP2015/002296 dated Feb. 10, 2017.
Ebbers E. J. et al., "Controlled Racemization of Optically Active Organic Compounds: Prospects for Asymmetric Transformation," Tetrahedron, Elsevier Science Publishers, Jul. 14, 1997, vol. 53, No. 28, pp. 9417-9476.
Muneer Ahamed et al., "The outcome of the oxidations of unusual Enediamide Motifs is Governed by the Stabilities of the intermediate iminium ions," PLOS ONE, Oct. 19, 2012, vol. 7, No. 10, p. e47224.

* cited by examiner

*Primary Examiner* — Erich A Leeser
(74) *Attorney, Agent, or Firm* — Millen White Zelano and Branigan, PC

(57) ABSTRACT

The present invention relates to a method for the racemization of enantiomerically pure or enantiomerically enriched Praziquantel under basic conditions and a method for the production of (R)-Praziquantel in enantiopure or enantiomerically enriched form, which comprises the racemization method.

9 Claims, No Drawings

METHOD FOR THE PRODUCTION OF PRAZIQUANTEL

FIELD OF THE INVENTION

The present invention relates to a method for the racemization of enantiomerically pure or enantiomerically enriched Praziquantel using basic conditions and to a method for the production of Praziquantel in enantiopure or enantiomerically enriched form, which comprises the racemization method.

BACKGROUND OF THE INVENTION

The anthelmintic Praziquantel has been registered, approved and commercialized in the beginning of the 80's of the last century as a racemate. However, the active molecule (eutomer) is the (R)-enantiomer (P. Andrews, H. Thomas, R. Pohlke, J. Seubert Medical Research Reviews 3, 147(1983)).

Racemic Praziquantel is available by a plethora of processes (see Domling et al. ChemMedChem 2010, 5, 1420-1434). The most developed technical scale processes are the original Merck process and the Shing-Poong process or one of its modifications. The racemic Praziquantel has a repugnantly bitter taste. This leads to acceptance issues—in particular in the treatment of young children. The (R)-Praziquantel eutomer is considered to have a less bitter taste than the (S)-Praziquantel distomer (T. Meyer et al. (2009) PLoS Negl Trop Dis 3(1): e357). Thus, there is a strong demand for a cost efficient manufacturing process for enantiomerically pure (R)-Praziquantel.

Many efforts were spent in the last decades to develop a manufacturing process for (R)-Praziquantel or its analogues. These processes can be divided in two groups, firstly enantioselective synthesis routes and secondly methods using the racemic process in combination with a chiral resolution. So far, a few enantioselective processes have been reported, but all of them are laborious and costly.

Woelfie et al. describe a chiral resolution of the Praziquantel precursor Praziquanamine (1,2,3,6,7,11b-Hexahydro-pyrazino[2,1-a]isoquinolin-4-one) by (−)-dibenzoyl-L-tartaric acid (Resolution of Praziquantel, M. Woelfle, J-P. Seerden, J. de Gooijer, Krees Pouwer, P. Olliaro, M. H. Todd, (2011) PLoS Negl. Trop. Dis 5(9):e1260.doi:10.1371/journal.pntd.000260). This resolution achieves rather low yields due to the fact that two crystallization steps are necessary to reach sufficiently high optical purity. Another problem associated with this procedure is the laborious and time-consuming recycling of (S)-Praziquanamine which could be done using the sequence: acylation, oxidative dehydrogenation, hydrogenation and finally deacylation. Beside this, the recycling of (−)-dibenzoyl-L-tartaric acid causes problems, because it is prone to saponification and trans-esterification. Both aspects are particularly difficult on production scale.

Alberto Cedillo Cruz et al. Tetrahedron: Asymmetry (2014), 25(2), 133-140 describes a chromatographic separation of the diastereomers Naproxen-(R)/(S)-praziquanamide, ((11bS)- and (11bR)-[(2S)-2-(6-Methoxy-2-naphthalenyl)-1-oxopropyl]-1,2,3,6,7,11b-hexahydro-2-4H-pyrazino[2,1-a]isoquinolin-4-one which are synthesized from (S)-Naproxen-acidchloride and racemic Praziquanamine, on an achiral phase. In order to obtain the (R)-Praziquanamine the covalent bond in (11bR)-[(2S)-2-(6-Methoxy-2-naphthalenyl)-1-oxopropyl]-1,2,3,6,7,11b-hexahydro-2-4H-pyrazino[2,1-a]isoquinolin-4-one must be cleaved under drastic conditions (85%-phosphoric acid, 150° C.). This process is laborious and not economic. Furthermore there is no efficient recycling of the undesired (S)-Praziquanamine.

Racemic Praziquantel can be separated into its enantiomers by chromatography. Especially effective on large scale is simulated counter current (simulated moving bed) chromatography (Chi-Bung Chin et al. Journal of Chromatography A, 734 (1996) 247-258, J. Pharm. Sciences 93, 3039 (2004), J. Chrom 634, 215(1993)). The disadvantage of the chiral separation of a chiral API at the final stage is, that the unwanted enantiomer, the distomer, is waste, unless there exists a procedure for recycling. Besides the tedious and practically not applicable sequence: selective dehydrogenation (oxidation by sulfur, Ahmed Muneer et al. PLos One 7(10), e 47224, 2012) of (S)-Praziquantel followed by hydrogenation, there does not exist an easily applicable recycling procedure for (S)-Praziquantel.

DESCRIPTION OF THE INVENTION

It is an object of the present invention to provide an efficient method for the recycling of (S)-Praziquantel, which works reliably and cost effective even on large scale and which can be utilized in a method for the production of Praziquantel in enantiopure or enantiomerically enriched form.

This object has surprisingly been solved by a method for the racemization of enantiomerically pure or enantiomerically enriched Praziquantel according to formula (I):

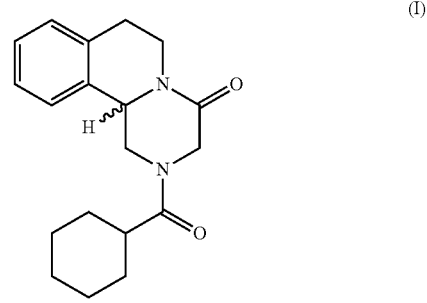 [SMILES: O=C(C1CCCCC1)N1CC(=O)N2CCc3ccccc3C2C1]

(I)

wherein a base used.

Praziquantel has a center of chirality and accordingly it occurs in two enantiomeric forms (S)-(I) and (R)-(I):

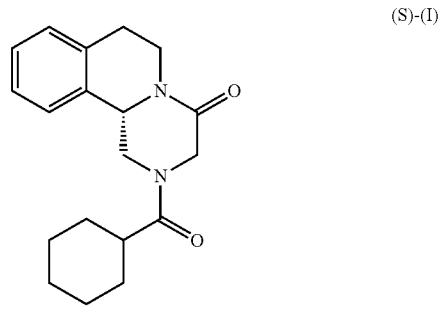

(S)-(I)

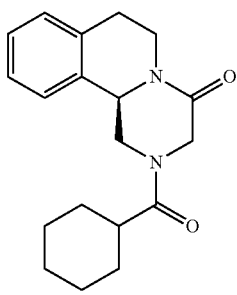 [SMILES: O=C(C1CCCCC1)N1CC(=O)N2CCc3ccccc3[C@@H]2C1]

(R)-(I)

The racemization method according to the invention provides a simple and efficient recycling process and is an economical prerequisite for preparing enantiomerically pure or enantiomerically enriched Praziquantel (in particular (R)-Praziquantel) by chiral separation of the racemate, which can be produced by known highly efficient processes. These existing processes (e.g. the Shin-Poong process or the original Merck process) are well established and highly optimized even on large scale.

For the purpose of the present invention the term "mixture of the enantiomers" includes racemic mixtures wherein the enantiomeric ratio is 50:50 as well as enantioenriched (enantiomerically enriched) mixtures. The term "enantiopure" (enantiomerically pure) means that one enantiomer is present in an optical purity of >95% ee, preferably >98% ee. Thus, the term "enantioenriched" (enantiomerically enriched) refers here to a mixture of the two enantiomers, wherein the enantiomeric ratio is larger than 50:50 but less than 97.5:2.5.

In principle, both enantiomeric forms (S)-(I) and (R)-(I) can be racemized with the process according to the invention. Though, obviously a particular important embodiment of the invention comprises methods, wherein the enantiomer used in the racemization is the (S)-enantiomer (S)-(I) of Praziquantel. In this case the process can be utilized to improve the process for the preparation of enantiopure or enantiomerically enriched (R)-Praziquantel by recycling the unwanted (S)-enantiomer of the product.

The method according to the invention includes processes where the starting material is racemized completely or partially. A partial racemization might be useful to keep side reactions low and such a procedure may still be efficiently used e.g. in cyclic procedures, where the racemization is combined with a chiral resolution step.

Much to our surprise we found, that enantiopure (R)- or (S)-Praziquantel racemizes, by treatment with appropriate bases under appropriate conditions. Different bases might be used to achieve appropriate basic conditions. However, it has been shown that a proper selection of the base is an important factor in view of possible side reactions, which usually lead to decomposition of the starting material.

A very important embodiment of the present invention comprises methods, wherein the base used for the racemization is a tertiary alkali alkoxide. Tertiary alkali alkoxides such as alkali tert.-butoxides or alkali tert.-pentoxides as well as their higher homologues are easily available standard reagents, but most of all, they allow to perform the racemization reaction with very good yield and with a low level of unwanted decomposition reactions. In a particular advantageous embodiment of the invention the tertiary alkali alkoxide is sodium or preferably potassium tert.-butoxide. This reagent allows performing the racemization with remarkably high yield within a very short reaction time.

In another specific embodiment of the present invention, the racemization is performed in a dipolar aprotic reaction medium such as e.g. ethers or N-Methyl-2-pyrrolidone, dimethylformamide or dimethylsulfoxide. In particular the dipolar aprotic reaction medium is selected form a group consisting of N-Methyl-2-pyrrolidone, dimethylformamide, dimethylsulfoxide, tetrahydrofuran, methyltetrahydrofuran, dioxane and mixtures thereof in all ratios. Suitable mixtures include for example mixtures of tetrahydrofuran and dimethylsulfoxide (in particular tetrahydrofuran in combination with 0.3 eq to 1.0 eq of dimethylsulfoxide), which might be useful to accelerate the racemization reaction. However, most preferably the dipolar aprotic medium is tetrahydrofuran. It was noted that unwanted side reactions can be reduced if the reaction mixture contains only little or no water (e.g. water content: 0.001%-0.1%).

Other parameters that influence the racemization reaction are the base stoichiometry and the temperature. Important embodiments of the invention comprise methods, wherein the amount of base used in the racemization process is in the range between 0.05 eq to 1.5 eq, preferably between 0.3 eq to 1.0 eq and most preferably between 0.4 eq to 0.8 eq. Furthermore the racemization is preferably performed at a temperature between −50° C. and +40° C., more preferably between −25° C. and +25° C., and most preferably between −20° C. and −5° C.

After all, a very specific embodiment of the invention refers to a method for the racemization of enantiomerically pure or enantiomerically enriched Praziquantel according formula (I) using basic conditions

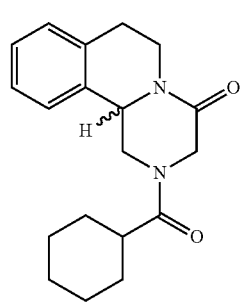

(I)

wherein
  a tertiary alkali alkoxide base is used for the racemization, preferably sodium or potassium tert.-butoxide and even more preferably potassium tert.-butoxide;
  the dipolar aprotic reaction medium is selected from a group consisting of N-Methyl-2-pyrrolidone, dimethylformamide, dimethylsulfoxide, tetrahydrofuran, methyltetrahydrofuran, dioxane and mixtures thereof in all ratios, preferably the reaction medium is tetrahydrofuran;
  the amount of base used in for the racemization is in the range between 0.05 eq to 1.5 eq, preferably 0.3 eq to 1.0 eq and most preferably 0.4 eq to 0.8 eq;

the racemization is performed at a temperature in the range between −50° C. and +40° C., preferably between −25° C. and +25° C., and most preferably between −20° C. and −5° C.

In this specific embodiment the enantiomer used in the racemization might be particularly (S)-Praziquantel. As indicated above, side reactions might be reduced if the reaction mixture contains only little or no water (e.g. water content: 0.001%-0.1%). It is preferred to utilize this specific racemization process to improve processes for the preparation of enantiopure or enantiomerically enriched (R)-Praziquantel based on an racemic approach by recycling the separated unwanted (S)-enantiomer of Praziquantel via racemization.

Another important aspect of the invention relates to a method for the production of (R)-Praziquantel in enantiopure or enantiomerically enriched form, comprising following steps:

a. Racemization of enantiomerically pure or enantiomerically enriched (S)-Praziquantel according to the invention as described above; and
b. Chiral resolution of the mixture of the enantiomers (S)-(I) and (R)-(I) obtained in a).

The combination of the racemization according to the invention with a chiral resolution step provides a very valuable recycling procedure, which might be performed only once within a production process according to the invention or several times in a row. The recycling of the unwanted enantiomer reduces waste and thus significantly improves the overall efficiency. The method according to the invention provides a simple and efficient process which can be utilized for the preparation of enantiopure or enantiomerically enriched (R)-Praziquantel, which can be integrated into existing very well established processes for the preparation of the racemic Praziquantel. Thus, a particular important embodiment of the invention comprises methods, wherein the (S)-enantiomer used in the racemization according to step a) is derived from a previously performed chiral resolution of a racemic mixture of Praziquantel obtained via a racemic synthesis route.

According to the invention the material obtained in racemization process a) might directly be applied in the chiral resolution step b), but might as well be purified in advance.

The chiral resolution of the compound according to formula (I) can be performed using different methods like e.g. chromatographic separation (in particular simulated bed chromatography (SMB). For example, the methods described in Chi-Bung Chin et al. Journal of Chromatography A, 734 (1996) 247-258, J. Pharm. Sciences 93, 3039 (2004), J. Chrom 634, 215(1993)) might be used.

EXPERIMENTAL SECTION

Abbreviations ee enantiomeric access
HPLC High Performance Liquid Chromatography
KOtBu potassium tert.-butoxide
mL Milliliter
(S)-PZQ (S)-Praziquantel
(R)-PZQ (R)-Praziquantel
RT Room Temperature
THF Tetrahydrofuran Example 1

Preparation of (R)-2-Cyclohexanecarbonyl-1,2,3,6,7,11b-hexahydro-pyrazino[2,1-a]isoquinolin-4-one ((R)-Praziquantel) via chiral resolution of the corresponding racemic mixture using HPLC

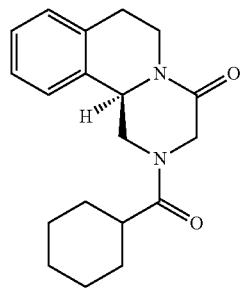

Racemic Praziquantel is well separable/resolvable with preparative chromatography using numerous chiral stationary phases. High productivity could be achieved after optimization of separation conditions.
Examples of Conditions:
Stationary phase: Chiralpak AD (20 μm)
Wave length: 230 nm
Eluent: Methanol
Stationary phase: Chiralpak ID (20 μm)
Wave length: 230 nm
Eluent: Acetonitrile/Methanol
Stationary phase: Chiralpak IA or IC (20 μm)
Wave length: 230 nm
Eluent Methanol/Dichloromethane Example 2

Racemization of (S)-Praziquantel 8.94 g (79.7 mmol) of potassium tert.-butoxide are dissolved under stirring in 150 mL dry THF under inert atmosphere (oxygen and moisture excluded). After cooling down to −10° C. a solution of 50 g (159.4 mmol) of (S)-Praziquantel (HPLC-purity 99.6%, ee=98.2% (S)) in 130 mL dry THF is dropwise added keeping the temperature lower than −7° C. After 4 h stirring at −10° C. the mixture is poured into an ice cold solution of 27 g (449.6 mmol) acetic acid in 300 mL deionized water. After stirring for further 30 min while leaving the solution warming up slowly to room temperature, 250 mL dichloromethane are added, the phases are separated and the aqueous layer is extracted two times with 150 mL dichloromethane. The combined organic layers are then washed with water and dried over sodium sulfate. After filtration and evaporation, 45.75 g (146.4 mmol) of a light orange crystalline residue are isolated and characterized as racemic Praziquantel (92% of theory, HPLC-purity 96.2%, ee=2.5% (R)).

Example 3

Racemization of (S)-Praziquantel Using Different Reaction Conditions

Table 1 exemplarily shows some results obtainable in the racemization of (S)-Praziquantel under different reaction conditions.

TABLE 1

| Starting Material | Solvent | Base | Temperature (° C.) | Time (min) | Result |
|---|---|---|---|---|---|
| (S)-PZQ 99% | THF | KOtBu 0.7 eq | −25 | 225 | (S)-PZQ 83% (R)-PZQ 16% Impurities 1% |
| (S)-PZQ 99% | THF | KOtBu 0.7 eq | RT | 220 | (S)-PZQ 29% (R)-PZQ 34% Impurities 36% |
| (S)-PZQ 99% | THF | KOtBu 0.7 eq | −15 | 180 | (S)-PZQ 71% (R)-PZQ 27% Impurities 2% |
| (S)-PZQ 99% | THF + 0.5 eq DMSO | KOtBu 0.8 eq | −15 | 165 | (S)-PZQ 50% (R)-PZQ 47% Impurities 3% |

The invention claimed is:

1. A method which comprises racemization of enantiomerically pure or enantiomerically enriched Praziquantel:

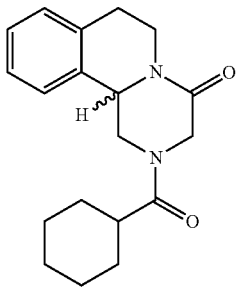

(I)

wherein a base is used and the base is a tertiary alkyl alkoxide.

2. A method according to claim 1, wherein the tertiary alkali alkoxide used for the racemization is potassium tert.-butoxide.

3. A method according to claim 1, wherein the racemization is a performed in a dipolar aprotic reaction medium.

4. A method according to claim 3, wherein the dipolar aprotic reaction medium is selected from the group consisting of N-Methyl-2-pyrrolidone, dimethylformamide, dimethylsulfoxide, tetrahydrofuran, methyltetrahydrofuran, dioxane and mixtures thereof in all ratios.

5. A method according to claim 1, wherein the racemization is performed at a temperature in a range between −50° C. and +40° C.

6. A method according claim 1, wherein the amount of base used for the racemization is in the range of 0.05 eq to 1.5 eq.

7. A method according to claim 1, wherein:
the racemization is performed in a dipolar aprotic reaction medium selected from a group consisting of N-Methyl-2-pyrrolidone, dimethylformamide, dimethylsulfoxide, tetrahydrofuran, methyltetrahydrofuran, dioxane and mixtures thereof in all ratios;
the amount of base used for the racemization is in the range between 0.05 eq to 1.5 eq;
the racemization is performed at a temperature in the range between −50° C. and +40° C.

8. A method for the production of (R)-Praziquantel in enantiopure or enantiomerically enriched form, comprising following steps:
a. Racemization of enantiomerically pure or enantiomerically enriched (S)-Praziquantel according to claim 1; and
b. Chiral resolution of the mixture of the enantiomers (S)-(I) and (R)-Praziquantel obtained in a).

9. A method according to claim 8, wherein the chiral resolution according to step b) is performed using chromatography.

* * * * *